United States Patent [19]
Ladd

[11] Patent Number: 5,792,109
[45] Date of Patent: Aug. 11, 1998

[54] IRRIGATION PUMP AND SYSTEM

[75] Inventor: Leland L. Ladd, 1080 McCarty, Dunedin, Fla. 34698

[73] Assignee: Leland L. Ladd, Dunedin, Fla.

[21] Appl. No.: 299,428

[22] Filed: Sep. 1, 1994

[51] Int. Cl.$^6$ .................................................. A61M 1/00
[52] U.S. Cl. ...................................... 604/151; 604/30
[58] Field of Search ................................ 604/131, 132, 604/133, 140, 141, 146, 65, 66, 67, 30, 31, 50, 246; 128/DIG. 12, DIG. 13

[56] References Cited

U.S. PATENT DOCUMENTS

| | | |
|---|---|---|
| 4,432,468 | 2/1984 | Siff et al. ............................. 604/65 |
| 4,613,327 | 9/1986 | Tegrarian et al. . |
| 4,657,160 | 4/1987 | Woods et al. . |
| 4,813,927 | 3/1989 | Morris et al. . |
| 4,976,687 | 12/1990 | Martin . |
| 4,998,914 | 3/1991 | Wiest et al. . |
| 5,057,076 | 10/1991 | Polaschegg ......................... 604/67 |
| 5,090,963 | 2/1992 | Gross et al. ................. 128/DIG. 12 |
| 5,171,301 | 12/1992 | Vanderveen ...................... 604/141 |
| 5,207,645 | 5/1993 | Ross et al. ........................ 604/141 |

*Primary Examiner*—Manuel Mendez
*Attorney, Agent, or Firm*—Waters & Morse, P.C.

[57] ABSTRACT

A medical irrigation pump and system for providing simultaneous controlled fluid flow from a plurality of reservoirs. The system is disposed to flow fluid sequentially from the reservoirs or to flow fluid simultaneously from two or more of them. This is accomplished by providing fluid in a plurality of bags or pliable containers which are then subjected to controlled pressures to force the fluid therefrom either simultaneously or sequentially, thereby providing versatility and enhanced liquid flow capability.

16 Claims, 4 Drawing Sheets

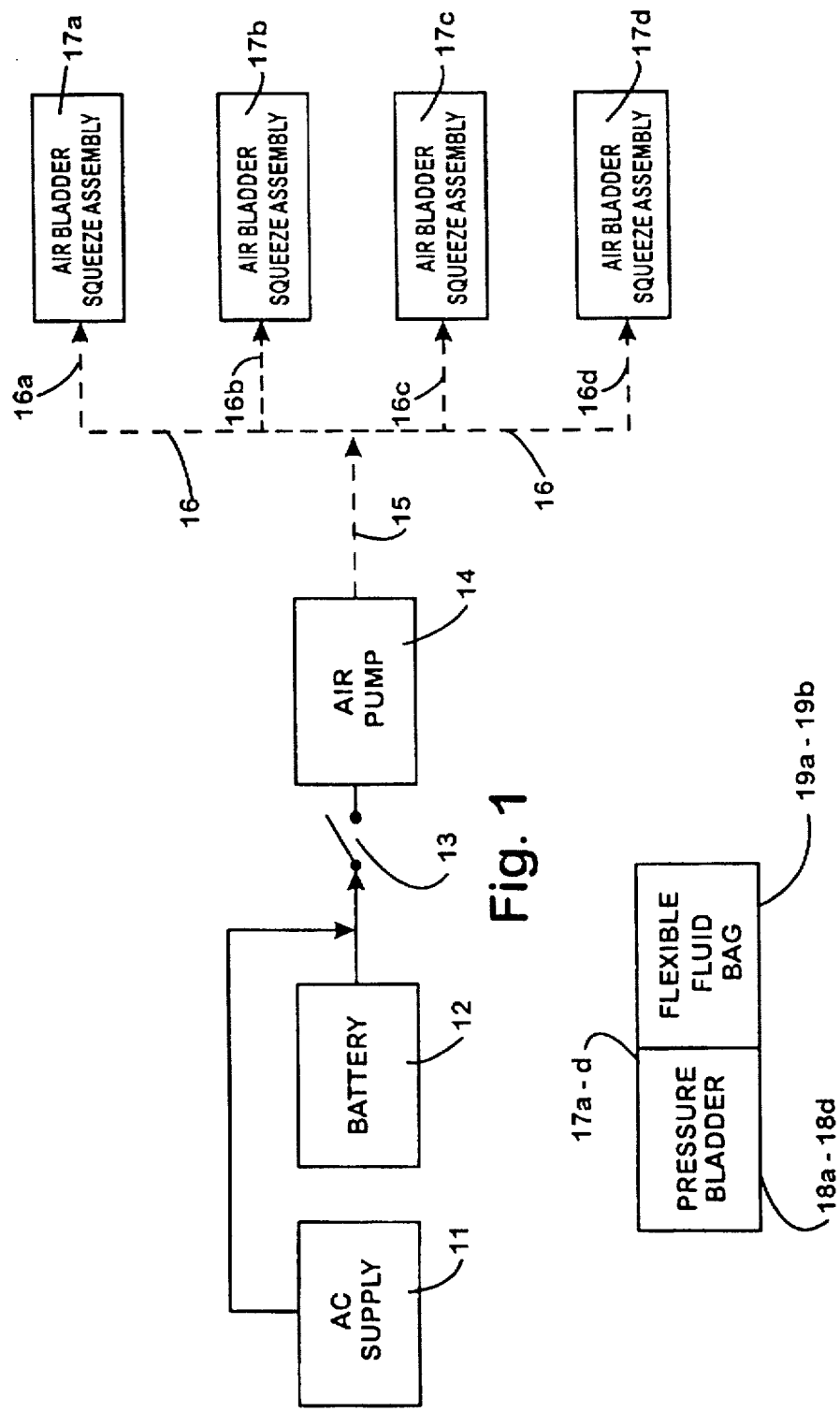

IRRIGATION PUMP AND SYSTEM

This invention relates to a system for medical irrigation and more particularly to such a system that provides a continuous controllable flow of irrigating fluids from a plurality of reservoirs.

BACKGROUND OF THE INVENTION

In the practice of medicine there arise numerous occasions when irrigation of a wound, incision or other body opening is necessary or desirable. Often, the required volume of irrigating fluid exceeds the capacity of a conventional source such as a one liter container. Moreover, it often is necessary or desirable to maintain the conditions of irrigation without interruption or change in the rate of fluid flow.

In the past, and in order to achieve continuous and uninterrupted flow of fluids, it has been proposed to enlarge the effective reservoir such as by providing piping from a common or central source. However, such has generally limited the variety of available irrigants or has introduced other problems such as increased vulnerability to contamination. In situations where the total quantity of fluid is small, it has been feasible simply to provide a control for the container in which such small quantity is supplied. An example of such control for fluids supplied for non-irrigation purposes is that disclosed in U.S. Pat. No. 4,657,160 granted to Andy Woods and Peter Giannini on Apr. 14, 1987. There, a pressure infusion system is disclosed in which a flexible bag containing a quantity of liquid to be infused is surrounded with a pressure cuff for causing the liquid to be forced from the bag. However, when the contents of the flexible bag are exhausted, it is necessary to replace the bag with another, thus occasioning temporary interruption of flow. Accordingly, there has continued to be a need for a system adapted for the utilization of a plurality of fluid sources and which provides continuous controlled and selectable flow.

BRIEF SUMMARY OF THE INVENTION

In accordance with the invention hereof, the foregoing continuous flow of fluids from a plurality of reservoirs is provided through the deployment of an improved control system that may be manipulated to individually, selectively and controllably pressurize a plurality of liquid reservoirs thus permitting continuous controlled liquid flow even when refilling or replacing liquid reservoirs. In combination with the foregoing, there are also provided pressure and flow rate alarms, pressure indicators, and immediate pressure release valves.

OBJECTS AND FEATURES OF THE INVENTION

It is one general object of the invention to improve medical irrigation systems.

It is another object of the invention to provide continuous flow of irrigating fluids from a plurality of reservoirs.

It is still another object of the invention to facilitate utilization of irrigating fluids from a plurality of reservoirs.

It is yet another object of the invention to facilitate use and adjustment of irrigation fluid controlling apparatus.

It is still another object of the invention to simplify manufacture and reduce cost of fluid controlling apparatus.

Accordingly, in accordance with one feature of the invention, a plurality of discrete flexible-walled pressurizable reservoirs are each fitted with a pressure cuff in physical engagement therewith, thereby providing an inexpensive and readily controllable sources of pressure to individually pressurize the reservoirs.

In accordance with another feature of the invention, a common source of pressure may be employed, thereby simplifying system air sourcing.

In accordance with yet another feature of the inventions, a pair of fluid flow and pressure vent (dump) controllers is provided for each pressure reservoir, thereby providing simplified individual control for fluid flow, rapid changeover and/or emergency shutdown.

In accordance with still another feature of the invention, in an alternate embodiment, provision is made for establishment and maintenance of predetermined pressure levels and/or fluid flow rates, thus contributing to the effectiveness of the apparatus.

In accordance with yet another feature of the invention, and in an alternate embodiment, provision is made for system sensing and control through the utilization of sensors.

These and other objects and features of the invention will be apparent from the following detailed description of the invention, by way of preferred embodiments, with reference to the drawings.

BRIEF DESCRIPTION OF THE DRAWING

FIG. 1 is a block diagram illustrating a general system according to the principles of the invention;

FIG. 1A is a block diagram illustrating the paired relationship of pressure bladders and flexible fluid bags in accordance with the invention;

DESCRIPTION OF A PREFERRED EMBODIMENT

Figure 2A:
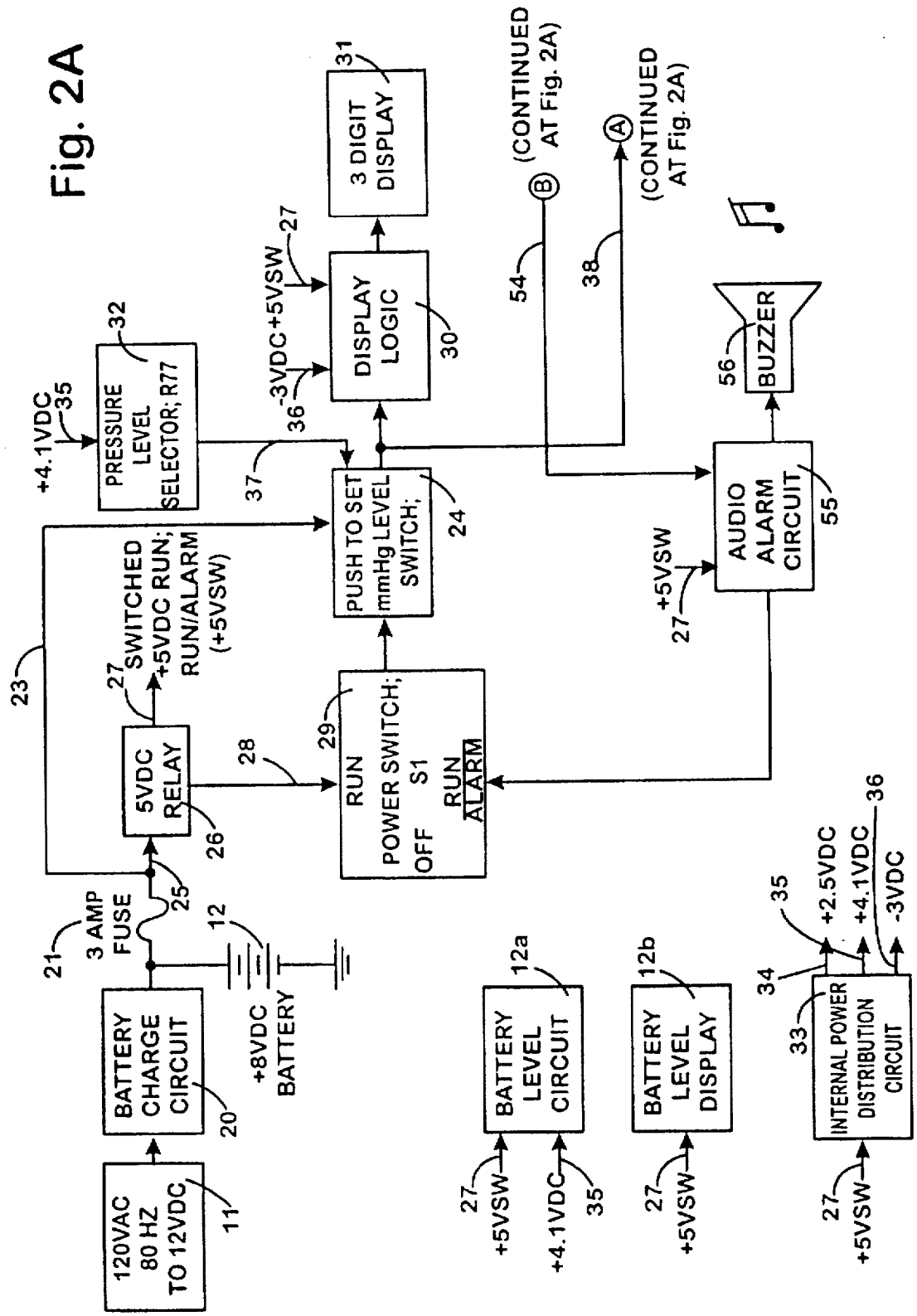
FIG. 2 is a more detailed diagram illustrating the preferred system according to the invention.

Now turning to FIG. 1, it will be seen to show a general system illustrating basic system components. There, it will be seen is a power source which may be conventional alternating current supply 11 or a battery 12 connected through a conventional electrical switch 13 to air pump 14. Air pump 14 is connected pneumatically through conventional tubing 15 to air header 16 which in turn is connected via header extensions 16a–16d to air bladder squeeze assemblies 17a–17d. As will be understood by those skilled in the art, components 11–16 are conventional off-the-shelf components and are readily available through a variety of commercial suppliers.

As illustrated in FIG. 1A, the air bladder squeeze assemblies (e.g. 17a–17d) are each comprised of a pressure bladder or cuff 18 in engagement with a flexible irrigation fluid bag 19 to which pressure is communicated when the pressure bladder is inflated. In accordance with the preferred embodiment hereof, the pressure bladders of squeeze assemblies 17a–17d are similar to conventional blood pressure cuffs which are generally available from a variety of commercial sources.

As mentioned above, FIG. 2 is a more detailed diagram illustrating a battery powered embodiment of the preferred system according to the invention. There are seen conventional alternating current source 11 connected to conventional battery charge circuits 20 that, in accordance with principles well known in the art, maintain operating charge on battery 12. Leading from the battery charge and battery supply circuit is a serially interposed circuit protective device such as a circuit breaker or fuse 21. From there circuits lead via path 23 to "push-to-set" pressure level switch 24 and via lead 25 to relay 26. There, it is seen to be connected via path 27 to provide power to several system components as shown in the drawing.

Relay 26 is connected via path 28 so as to be under the control of Run Power/Alarm switch assembly 29. Thus, Run Power/Alarm switch assembly 29 acts as a master switch that is used to start and stop system operation. When it is desired to activate the system, a conventional electrical switch S1 in assembly 29 is actuated to operate relay 26 and to begin system operation.

It should be noted that path 23 provides power for switch 24 irrespective of whether or not power switch S1 in switch assembly is on or off, thus providing for activation of conventional display logic 30 so that it may be set for the desired pressure level in advance of production of air pressure by pump 14. Provision is also made for energization of 3-digit conventional pressure display so that it is powered up and ready to display pressure as soon as main power switch S1 (module 29) is turned on. Moreover, a desired pressure level may be set in advance through conventional pressure level selector 32.

It will be observed from reference to Internal Power Distribution Circuit 33 that when relay 26 is closed, provision is made for producing three levels of direct current voltage: (1) +2.5 Volts; (2) +4.1 Volts; and (3) −3 Volts which are represented respectively by arrows 34, 35 and 36. These are applied to various ones of the remaining circuit modules as identified by correspondingly numbered inputs. Thus, turning on of main power switch S1 and closing of relay 26 provides energy at the different voltage levels needed to operate the system.

Returning now to "Push-to-Set" Pressure Level Switch 24, it will be seen that it is connected via path 37 to pressure level selector 32. Thus, when it is desired to set the desired level of air pressure in air header 16, a conventional push button in switch module 24 is depressed and the desired level of pressure is selected by manipulation of conventional Pressure Level Selector 32. As the level is being selected, its value is displayed through logic 30 and display 31. When the selected level is accepted by the operator, its value is communicated via path 38 to pressure logic module 40 whence it is effective via path 41 to condition pump control module 42 which in turn is effective via path 43 to control conventional pump 14.

Since noise reduction is particularly important in medical environments, provision is made for muffling the sound of air as it enters the pump intake. This is accomplished by muffler which is shown connected to pump 14 by input manifold 45.

Returning to Pressure Logic 40, it will be seen that it is additionally controlled by Pressure Sensor Circuit Module 46 which is connected to air header 16 via paths 47 and 48. Thus, when pressure in header 16 is less than the selected value, module 46 communicates such to pressure logic 40 via path 49, thus resulting in pump control 42 to correspondingly condition pump 14.

In order to provide for safe operation of the equipment, an over pressure limit switch 50 is provided to sense air header pressure via path 47. If such pressure rises to a predetermined level, then pump control 42 is overridden via path 51 and the pump is instantaneously shut down. At the same time, an alarm signal is conducted via path 52 to visual alarm circuit 53 where it activates a visual alarm and sends a signal via path 54 to activate audio alarm circuit 55 and optional buzzer 56.

In addition to the foregoing, an additional level of alarm and control is represented by paths 57 and 58 which interconnect Pressure Logic module 40 with Visual Alarm Circuit module 53 and Pressure Sensor Circuit module 46.

Figure 2B:
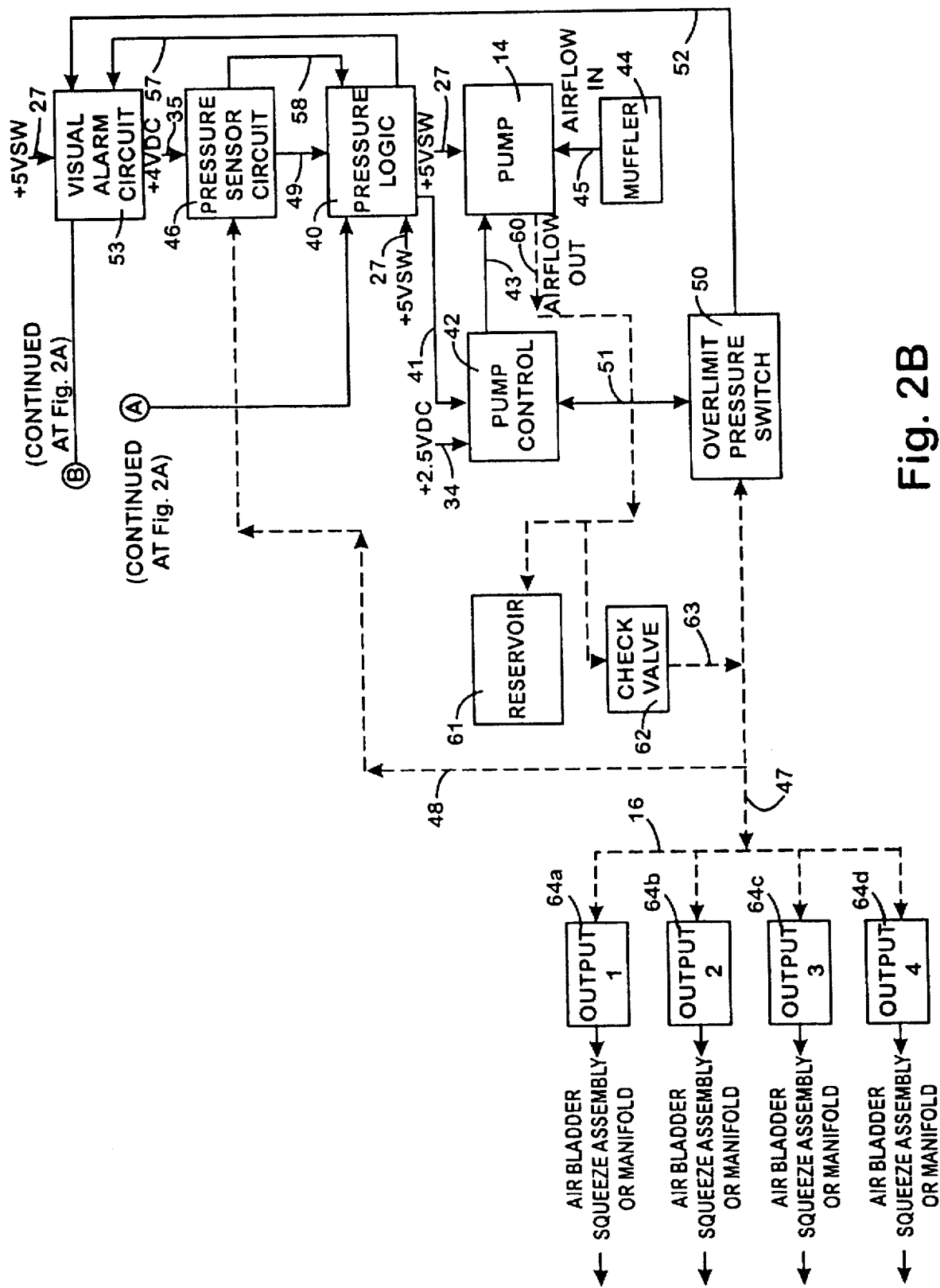

Further reference to FIG. 2 reveals the presence of Pump Air Outflow conduit 60 which connects pump 14 with Reservoir 61 and conventional check valve 62 whence air is introduced via conduit 63 to conduit 47 whence it is communicated to air header 16. Air header 16 in turn is preferably connected to four outputs 64a–64d which in turn are connected to four air bladders such as bladders 17a–17d (FIGS. 1 and 3) directly or preferably through an air management manifold such as manifold 70 (FIG. 3).

Provision is optionally but preferably made for inclusion of battery monitoring and display circuits. These are conventional and are represented by items 12a and 12b. Inclusion of a battery condition display on the system display panel adds to the usefulness and dependability of the equipment.

Figure 3:
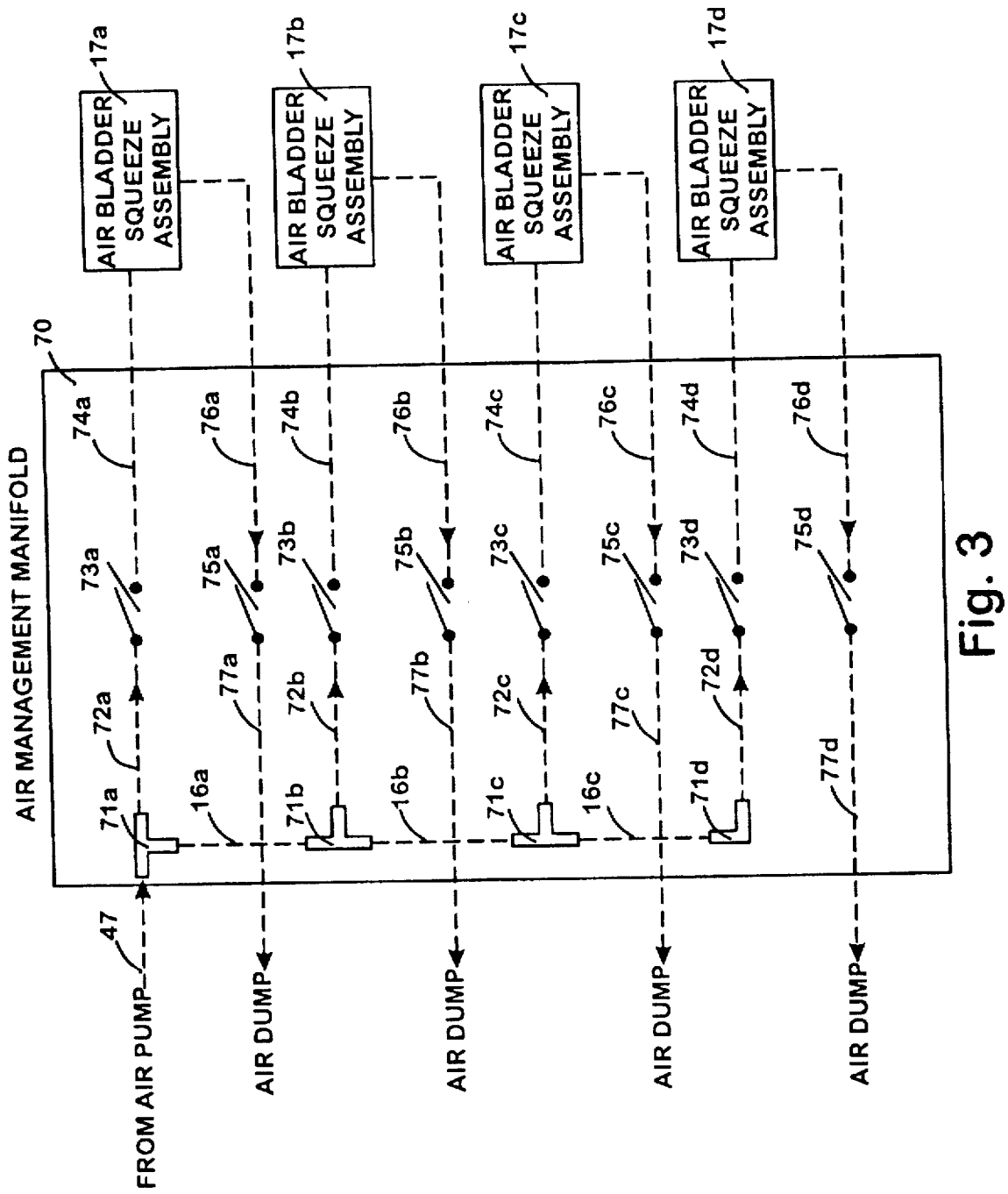
FIG. 3 is a block diagram illustrating an air management manifold according to the invention.

Now turning to FIG. 3, it will be seen schematically to depict Air Management Manifold 70 which is a module of air conduits, valves and connectors. Air input to the manifold is represented by conduit 47 which in turn is connected to a header corresponding to header 16 in FIGS. 1 and 2 and including branches 16a–16c connected through T's and an elbow 71a–71d. Extending from these T's and elbows are individual air conduits 72a–72d which include serially interposed air valves represented by switch symbols 73a–73d, thus providing for individual control of air passing through conduits 72a–72d.

Leading from the downstream side of air valves 73a–73b are individual air conduits 74a–74d which lead respectively to discrete and separate air bladder squeeze assemblies 17a–17d each of which includes an air pressure bladder or cuff such as item 18 in FIG. 1A together with a flexible fluid bag such as item 19 in FIG. 1A. However in contrast with FIGS. 1 and 1A, there is provided in FIG. 3 a series of individual pressure dump valves 75a–75d, the upstream portions 76a–76d of which are in communication with air in pressure bladders 18a–18d (FIG. 1A); and the downstream portions 77a–77d being directed to any suitable air dump environment. Ordinarily, the air dump environment is the location in which the equipment is used. However, in certain circumstances it may be desired to vent the air dump to some predetermined location, in which event a hose or other conduit may be connected to the air dump terminals.

The foregoing air dump valves 75a–75d may be manually operated and/or electrically controlled as by connection to the pressure logic circuits 40 of FIG. 2. Any of a variety of valves well known in the art may be employed.

It will now be evident to those skilled in the art that there has been described herein an improved automatic pump and air ballast squeeze system that provides a number of features including provision for individual control of a plurality of flexible bags together with fluid flow control, ability to change bags without fluid flow interruption, and over/under pressure alarm or shut-down.

Although the invention hereof has been described by way of example of preferred embodiments, it will be evident that other adaptations and modifications can be employed without departing from the spirit and scope thereof. For example, alternatives may be employed for the squeeze bag assemblies.

The terms and expressions employed herein have been used as terms of description and not of limitation; and thus, there is no intent of excluding equivalents, but on the contrary it is intended to cover any and all equivalents that may be employed without departing from the spirit and scope of the invention.

What is claimed is:

1. A medical irrigation system comprising:
   (a) a plurality of flexible enclosed reservoirs containing predetermined medical liquids;
   (b) fluid conducting means for selectively conducting flow of said medical liquids from said reservoirs to a first predetermined location;
   (c) a first air bladder in pressure communication with a first one of said reservoirs for controlling pressure within said first one of said reservoirs;
   (d) a second air bladder in pressure communication with a second one of said reservoirs for controlling pressure within said second one of said reservoirs; and
   (e) means connected to said first and second air bladders for independently pressurizing said first and second air bladders thereby to selectively and correspondingly pressurize said liquids.

2. A medical irrigation system according to claim 1 in which said pressurizable reservoirs are enclosed.

3. A medical irrigation system according to claim 1 in which said first and second ones of said reservoirs are discrete and separate.

4. A medical irrigation system according to claim 1 in which said first and second air bladders are connected to a single pressure pump.

5. A medical irrigation system according to claim 1 in which said fluid in said first one of said reservoirs is identical to said fluid in said second one of said reservoirs.

6. A medical irrigation system according to claim 1 in which said fluid conducting means is adapted to simultaneously conduct said fluids from said reservoirs to said first predetermined location.

7. A medical irrigation system according to claim 1 in which said fluid conducting means is adapted to sequentially conduct said fluids from said reservoirs to said first predetermined location.

8. A medical irrigation system according to claim 1 in which said control means includes a control panel interconnected with said reservoirs, said control panel having a display for displaying pressure in each of said reservoirs.

9. A medical irrigation system according to claim 1 further including, in combination, a self-contained power supply interconnected with said control means for supplying energizing power to said control means from a battery.

10. A medical irrigation system according to claim 1 further including a pair of pressure dump valves severally interconnected with said first and said second air bladders effective when activated for selectively, individually and immediately releasing pressure from said bladders.

11. A medical irrigation system according to claim 10 further including:

(a) alarm means; and
(b) pressure sensing means responsive to unintentional release of pressure within one of said reservoirs for activating said alarm means.

12. A medical irrigation system according to claim 1 further including:
(a) alarm means; and
(b) pressure sensing means responsive to unintentional release of pressure within one of said reservoirs for activating said alarm means.

13. A medical irrigation system according to claim 12 further including means for setting and maintaining constant said pressures within said reservoirs.

14. A medical irrigation system according to claim 12 further including means responsive to unintentional cessation of said flow of said medical liquids for activating said alarm means.

15. A medical irrigation system according to claim 1 further including means for setting and maintaining constant said pressures within said reservoirs.

16. A medical irrigation system comprising:
   (a) a plurality of flexible enclosed reservoirs containing predetermined medical liquids;
   (b) fluid conducting means for selectively conducting said medical liquids from said reservoirs to a first predetermined location;
   (c) a first air bladder in pressure communication with a first one of said reservoirs for controlling pressure within said first one of said reservoirs;
   (d) first pressure release means connected to said first air bladder for immediate release of pressure from said first air bladder;
   (e) a second air bladder in pressure communication with a second one of said reservoirs for controlling pressure within said second one of said reservoirs;
   (f) second pressure release means connected to said second air bladder for immediate release of pressure from said said second bladder;
   (g) means connected to said first and second air bladders for normally pressurizing said first and second air bladders thereby to selectively and correspondingly pressurize said liquids;
   (h) means for selectively setting and maintaining constant said pressures within each of said reservoirs;
   (i) alarm means;
   (j) pressure sensing means responsive to unintentional release of pressure within one of said reservoirs for activating said alarm means; and
   (k) liquid flow sensing means responsive to unintentional cessation of liquid flow for activating said alarm means.

* * * * *